United States Patent [19]

Wirtz et al.

[11] Patent Number: 5,476,963

[45] Date of Patent: Dec. 19, 1995

[54] SUPPORTED CATALYST, PROCESS FOR ITS PREPARATION AND ITS USE FOR THE PREPARATION OF VINYL ACETATE

[75] Inventors: Peter Wirtz, Königstein; Friedrich Wunder, Hattersheim am Main; Karl-Fred Wörner, Eschborn, all of Germany

[73] Assignee: Hoechst AG, Frankfurt, Germany

[21] Appl. No.: 394,840

[22] Filed: Feb. 27, 1995

Related U.S. Application Data

[62] Division of Ser. No. 43,567, Apr. 7, 1993, Pat. No. 5,442,329.

[30] Foreign Application Priority Data

Apr. 8, 1992 [DE] Germany ............ 42 11 780.1

[51] Int. Cl.⁶ .................. C07C 69/15; C07C 67/05
[52] U.S. Cl. ............................. 560/241; 560/245
[58] Field of Search ...................... 560/241, 231, 560/232, 245

[56] References Cited

U.S. PATENT DOCUMENTS

| | | | |
|---|---|---|---|
| 3,393,199 | 7/1968 | Daum et al. | 260/294.9 |
| 3,775,348 | 11/1973 | Jakobi et al. | 252/324 |
| 4,048,096 | 9/1977 | Bissot | 560/231 |
| 4,668,819 | 5/1987 | Fernholz et al. | 560/245 |
| 4,902,823 | 2/1990 | Wunder et al. | 560/245 |
| 5,066,365 | 11/1991 | Roscher et al. | 203/42 |
| 5,130,286 | 7/1992 | Michaels et al. | 502/340 |
| 5,354,886 | 10/1994 | Park et al. | 560/232 |
| 5,371,274 | 12/1994 | Park et al. | 560/232 |

FOREIGN PATENT DOCUMENTS

| | | |
|---|---|---|
| 0154408 | 9/1985 | European Pat. Off. |
| 2223355 | 3/1974 | France. |
| 2745174 | 4/1979 | Germany. |
| 1267354 | 3/1972 | United Kingdom. |

*Primary Examiner*—Arthur C. Prescott
*Attorney, Agent, or Firm*—Connolly & Hutz

[57] ABSTRACT

Supported catalyst, process for its preparation and its use for the preparation of vinyl acetate The invention relates to improved Pd/K/Au, Pd/K/Ba and Pd/K/Cd supported catalysts, their preparation and their use for the preparation of vinyl acetate from ethylene, acetic acid and oxygen in the gas phase. The stated catalysts are prepared by atomizing a solution of corresponding metal salts by means of ultrasonics and then applying them in such limited amounts and within such a limited time to the carrier particles, and beginning to dry them, so that the catalytically active metal salts cannot penetrate into the carrier particles as far as the core but only into a larger or smaller outer part.

6 Claims, No Drawings

SUPPORTED CATALYST, PROCESS FOR ITS PREPARATION AND ITS USE FOR THE PREPARATION OF VINYL ACETATE

This is a divisional of Ser. No. 0/043,567, filed Apr. 7, 1993 now U.S. Pat. No. 5,442,329.

It is known that vinyl acetate can be prepared in the gas phase from ethylene, acetic acid and oxygen; the supported catalysts used for this synthesis contain palladium and an alkali metal element, preferably potassium. Further additives used are cadmium, gold or barium.

In the Pd/K/Au catalysts, the two noble metals are generally applied in the form of a coat to the carrier; the preparation is carried out by impregnation and subsequent precipitation of the metal salts by means of alkaline compounds (U.S. Pat. No. 4,048,096 and U.S. Pat. No. 3,775, 342).

In Pd/K/Ba catalysts, the metal salts are applied by soaking, spraying, vapor deposition, immersion or precipitation (German Patent Application P 41 20 491.3). The same methods are known in the case of Pd/K/Cd catalysts (U.S. Pat. No. 4,902,823; U.S. Pat. No. 3,393,199 and U.S. Pat. No. 4,668,819); the preparation of a coated catalyst is also described here, a special carrier material being washed with an acid prior to impregnation and being treated with a base after impregnation (German Patent Application P 41 20 492.1).

Surprisingly, it has now been found that improved Pd/K/Au, Pd/K/Ba or Pd/K/Cd catalysts are obtained when a solution of corresponding metal salts is atomized by means of ultrasonics and then applied in such limited amounts and within such a limited time to the carrier particles and drying thereof is begun that the catalytically active metal salts cannot penetrate into the carrier particles as far as the core but only into a larger or smaller outer part. This means that the solution atomized by ultrasonics is applied in such a way that a coat is formed. Surprisingly, these kind of coated catalyst has a substantially improved selectivity as well as performance or specific performance in the preparation of vinyl acetate, which surpasses not only the corresponding values of the catalysts according to U.S. Pat. No. 4,902,823 which have been fully impregnated (through to the core) but also the values of the coated catalysts prepared by other means (U.S. Pat. No. 4,048,096, U.S. Pat. No. 3,775,342, German Patent Application P 41 20 492.1.

The invention relates to a process for the preparation of a supported catalyst containing palladium, potassium and cadmium, which comprises dissolving salts of palladium, of potassium and of cadmium in a suitable solvent, atomizing the solution by ultrasonics, impregnating the carrier material once or repeatedly with the atomized solution and drying it after each impregnation, the solution volume for each impregnation being at least 5 to at most 60% of the pore volume of the carrier material and the duration of each impregnation and the time up to the beginning of the drying which follows this impregnation being chosen to be so short that, after the end of the final drying, a coat of at least 5 to at most 60% of the volume of the carrier particles contains the stated salts. The invention furthermore relates to a supported catalyst prepared in this manner and to its use for the preparation of vinyl acetate from ethylene, acetic acid and oxygen in the gas phase.

The solution volume for each impregnation with the Pd, K and Cd salts is preferably at least 5 to at most 50% of the pore volume of the carrier material, in particular at least 15 to at most 40% of the pore volume, the duration of each impregnation and the time up to the beginning of the drying which follows this impregnation being chosen to be so short that, after the end of the final drying, a coat of at least 5 to at most 50% of the volume of the carrier particles contains the stated salts—in particular a coat of at least 15 to at most 40% of the volume of the carrier particles.

The invention furthermore relates to a process for the preparation of a supported catalyst containing palladium, potassium and barium, which comprises dissolving salts of palladium, of potassium and of barium in a suitable solvent, atomizing the solution by ultrasonics, impregnating the carrier material once or repeatedly with the atomized solution and drying it after each impregnation, the solution volume for each impregnation being at least 15 to at most 80% of the pore volume of the carrier material and the duration of each impregnation and the time up to the beginning of the drying which follows this impregnation being chosen to be so short that, after the end of the final drying, a coat of at least 15 to at most 80% of the volume of the carrier particles contains the stated salts. The invention furthermore relates to a supported catalyst prepared in this manner and to its use for the preparation of vinyl acetate from ethylene, acetic acid and oxygen in the gas phase.

The solution volume for each impregnation with the Pd, K and Ba salts is preferably at least 20 to at most 80% of the pore volume of the carrier material, in particular at least 25 to at most 40% of the pore volume, the duration of each impregnation and the time up to the beginning of the drying which follows this impregnation being chosen to be so short that, after the end of the final drying, a coat of at least 20 to at most 80% of the volume of the carrier particles contains the stated salts—in particular a coat of at least 25 to at most 40% of the volume of the carrier particles.

The invention furthermore relates to a process for the preparation of a supported catalyst containing palladium, potassium and gold, which comprises dissolving salts of palladium, of potassium and of gold in a suitable solvent, atomizing the solution by ultrasonics, impregnating the carrier material once or repeatedly with the atomized solution and drying it after each impregnation, the solution volume for each impregnation being at least 5 to at most 80% of the pore volume of the carrier material and the duration of each impregnation and the time up to the beginning of the drying which follows this impregnation being chosen to be so short that, after the end of the final drying, a coat of at least 5 to at most 80% of the volume of the carrier particles contains the stated salts. The invention furthermore relates to a supported catalyst prepared in this manner and to its use for the preparation of vinyl acetate from ethylene, acetic acid and oxygen in the gas phase.

The solution volume for each impregnation with the Pd, K and Au salts is preferably at least 10 to at most 60% of the pore volume of the carrier material, in particular at least 15 to at most 50% of the pore volume, the duration of each impregnation and the time up to the beginning of the drying which follows this impregnation being chosen to be so short that, after the end of the final drying, a coat of at least 10 to at most 60% of the volume of the carrier particles contains the stated salts—in particular a coat of at least 15 to at most 50% of the volume of the carrier particles.

Inert materials, such as silica, alumina or mixtures of these oxides, in the form of spheres, pellets, rings, stars or other moldings are used as carriers; the diameter or the length and thickness of the carrier particles is or are in general between 4 and 15 mm.

The surface area of the carrier is in general 40 to 300 $m^2/g$, measured by the BET method; the pore volume is in general 0.5 to 1.0 ml/g.

The metal contents of the prepared catalysts have the following values:

The palladium content of the Pd/K/Cd and of the Pd/K/Ba catalysts is in general 0.6 to 3.5% by weight, preferably 0.8 to 3.0% by weight, in particular 1.0 to 2.5% by weight. The palladium content of the Pd/K/Au catalysts is in general 0.5 to 2.0% by weight, preferably 0.6 to 1.5% by weight.

The potassium content of all three catalyst types is in general 0.5 to 4.0% by weight, preferably 1.5 to 3.0% by weight.

The cadmium content of the Pd/K/Cd catalysts is in general 0.1 to 2.5% by weight, preferably 0.4 to 2.0% by weight.

The barium content of the Pd/K/Ba catalysts is in general 0.1 to 2.0% by weight, preferably 0.2 to 1.0% by weight. The gold content of the Pd/K/Au catalysts is in general 0.2 to 1.0% by weight, preferably 0.3 to 0.8% by weight.

Suitable salts are all salts of palladium, cadmium, barium, gold and potassium which are soluble and do not contain any components which are poisonous to the catalyst, such as, for example, sulfur; the acetates and the chlorides are preferred. However, in the case of the chlorides, it must be ensured that the chloride ions are removed before the catalyst is used. This is effected by washing out the doped carrier, for example with water, after the palladium and, where relevant, gold have been converted into an insoluble form, for example by reduction.

Suitable solvents are all compounds in which the selected salts are soluble and which can readily be removed again by drying after the impregnation. In particular, unsubstituted carboxylic acids having 2 to 10 carbon atoms, such as acetic acid, propionic acid, n-butyric acid and isobutyric acid and the various valeric acids, are suitable for the acetates. Owing to its physical properties and also for economic reasons, acetic acid is preferred among the carboxylic acids. Water is particularly suitable for the chlorides. The additional use of a further solvent is advantageous when the salts are not sufficiently soluble in the acetic acid or in water. Suitable additional solvents are those which are inert and are miscible with acetic acid or water. Ketones, such as acetone and acetylacetone, and ethers, such as tetrahydrofuran or dioxane, as well as hydrocarbons, such as benzene, may be mentioned as additives for acetic acid.

According to the invention, the solution of the salts is atomized by ultrasonics. The frequency of the ultrasonics is preferably 30 to 200 kHz, preferably 80 to 200 kHz. Suitable apparatuses for this atomization are commercially available under the name "Ultraschall-Flüssigkeitszerstäuber" or "Ultrasonic Atomizer" or "Ultrasonic Nebulizer" (for example from the manufacturers Siemens AG, Erlangen, or Lechler, Metzingen, Germany).

During the ultrasonic atomization, the solution of the salts should have a temperature which is sufficiently high to prevent precipitation of the salts during application to the carrier. In general, however, the temperature should not be substantially above 70° C. in order to prevent excessive evaporation of the solvent.

The duration of the impregnation must on the one hand be so short that a coat forms which accounts for at least 5 to at most 60% of the pore volume of the carrier particles in the case of the Pd/K/Cd catalysts, or at least 5 to at most 80% in the case of the Pd/K/Au catalysts and at least 15 to at most 80% in the case of the Pd/K/Ba catalysts. On the other hand, the duration of the impregnation must be sufficiently long to ensure a uniform coat thickness of all carrier particles. The optimum duration is dependent on the amount of the salts, on the amount of the solvent and on the amount of the carrier material to be impregnated; however, it can be readily determined by preliminary experiments. A suitable method for determining the resulting distribution of the coat thickness is to cut open a representative number of carrier particles and measure the coat thickness under a microscope. In general, less than 5% of the particles should have a coat thickness which differs from the mean by more than 15%.

During the impregnation, it is advisable to ensure uniform thorough mixing of the carrier particles, for example by employing a rotating flask or a mixing drum. The rotational speed must on the one hand be sufficiently high to ensure thorough mixing but on the other hand must not be so high that substantial abrasion of the carrier material occurs. For a batch size of 1 liter of carrier material, a rotational speed of 100 to 200 revolutions/minute has proven suitable in a 10 l flask.

During drying of the carrier impregnated with the solution of the active catalyst components, it is advisable to adapt the temperature to the type of metal salts used. In the case of the acetates, which are frequently used for the preparation of Pd/K/Cd or Pd/K/Ba catalysts, drying is preferably carried out under reduced pressure. The temperature should be in general 50° to 80° C., preferably 50° to 70° C. It is also advisable in general to carry out the drying in an inert gas stream, for example in a nitrogen or carbon dioxide stream. In the case of the Pd/K/Au catalysts impregnated in general with the corresponding chlorides, drying can, on the other hand, be carried out in a hot air stream at 100° to 150° C. The residual solvent content after drying should preferably be less than 6% by weight for all three catalyst types.

If a reduction of the palladium salt and, if required, the gold salt is carried out, this being useful in some cases, this may be effected by means of a gaseous reducing agent. The reduction temperature is in general between 40° and 260° C., preferably between 70° and 200° C. In general, it is advantageous to use, for the reduction, a reducing agent which is diluted with inert gas and contains 0.01 to 50% by volume, preferably 0.5 to 20% by volume of a reducing agent. For example, nitrogen, carbon dioxide or a noble gas can be used as the inert gas. Suitable reducing agents are, for example, hydrogen, methanol, formaldehyde, ethylene, propylene, isobutylene, butylene or other olefins. The amount of the reducing agent depends on the amount of palladium and, where relevant, on the amount of gold; the reduction equivalent should be at least 1 to 1.5 times the oxidation equivalent, but larger amounts of the reducing agent have no adverse effect. Such a reduction is carried out after the drying.

The preparation of the vinyl acetate is carried out in general by passing acetic acid, ethylene and oxygen or oxygen-containing gases at temperatures of 100° to 220° C., preferably 120° to 200° C., and at pressures of 1 to 25 bar, preferably 1 to 20 bar, over the prepared catalyst, it being possible to circulate unconverted components. The oxygen concentration is advantageously kept below 10% by volume (based on the gas mixture free of acetic acid). Under certain circumstances, however, dilution with inert gases, such as nitrogen or carbon dioxide, is also advantageous. Carbon dioxide is particularly suitable for the dilution since it is formed in small amounts during the reaction.

With the aid of the catalysts according to the invention, a more selective procedure or an increase in capacity is possible. For an increase in capacity, it is possible to keep the reaction conditions (for example pressure, temperature, throughput and oxygen concentration) unchanged compared with the known catalysts and to prepare more vinyl acetate per reactor volume per unit time. Working up of the crude vinyl acetate obtained is thus facilitated since the vinyl acetate content of the gas emerging from the reactor is higher, which furthermore leads to an energy saving in the working up part. A suitable working up procedure is described, for example, in U.S. Pat. No. 5,066,365.

If, on the other hand, the plant capacity is kept constant, the reaction temperature can be reduced and the reaction can thus be carried out in a more selective manner with the same total output, starting materials being saved. Furthermore, the amount of carbon dioxide which is formed as a byproduct and therefore has to be removed and the loss of entrained ethylene associated with removal of the carbon dioxide are smaller. In addition, this procedure leads to an extension in the catalyst life.

The Examples below are intended to illustrate the invention.

The catalyst carrier used was $SiO_2$ in the form of pellets having a diameter and a height of 6 mm each. The pellets had been pressed from ®Aerosil powder with the aid of magnesium stearate as a binder, according to German Offenlegungsschrift 3,912,504. The surface area of the carrier was 120 $m^2$/g, its pore volume was 0.784 ml/g and its bulk density 500 g/l.

COMPARATIVE EXAMPLE 1

1 l of silica carrier was impregnated with a solution of 24.3 g of palladium acetate, 21.3 g of cadmium acetate and 23.8 g of potassium acetate in 392 ml of glacial acetic acid (solution volume=100% of the pore volume of the carrier) at 60° C. Drying was then carried out in a drying oven at 200 mbar under nitrogen to a residual acetic acid content of 6% by weight; the drying temperature was 65° C. The prepared catalyst contained 2.3% by weight of Pd, 1.8% by weight of Cd and 1.9% by weight of K.

50 ml of this catalyst were introduced into a reaction tube having an internal diameter of 8 mm and a length of 1.5 mm. The gas to be reacted was then passed over the catalyst at a pressure of 8 bar (reactor entrance) and a catalyst temperature of 150° C. This gas consisted of 27% by volume of ethylene, 55% by volume of nitrogen, 12% by volume of acetic acid and 6% by volume of oxygen. The results are shown in Table 1.

COMPARATIVE EXAMPLE 2

The catalyst preparation was carried out as in Comparative Example 1, except that 4.0 g of barium acetate were now applied instead of cadmium acetate. The prepared catalyst contained 2.3% by weight of Pd, 0.4% by weight of Ba and 1.9% by weight of K.

Testing was carried out as in Comparative Example 1; the results are shown in Table 1.

COMPARATIVE EXAMPLE 3

According to German Patent Application P 41 20 492.1, 1 l of silica carrier was washed with 10% strength hydrochloric acid and then with water in order to remove the binder which interferes with coat formation, and was then dried. The carrier was then impregnated with a solution of 12.5 g of palladium chloride and 16.5 g of cadmium chloride in 392 ml of water. After the drying with hot air at 150° C., 7.5 g of NaOH, dissolved in 392 ml of water, were added (in order to produce a coat by precipitating palladium and cadmium). Stirring was then carried out for 6 hours and the mixture was allowed to stand for 16 hours at room temperature. After the carrier had been washed chloride-free with water and dried with hot air at 150° C., 37.6 g of potassium acetate in 392 ml of water were applied. After drying with hot air at 150° C., the catalyst contained 1.5% by weight of Pd, 2.0% by weight of Cd and 3.0% by weight of K. The thickness of the coat produced by the treatment with sodium hydroxide solution was 1.5 to 1.7 mm. Testing was carried out as in Comparative Example 1. The results are shown in Table 1.

COMPARATIVE EXAMPLE 4

The catalyst preparation was carried out as in Comparative Example 3, except that 4.0 g of tetrachloroauric acid were used instead of cadmium chloride and 13.8 g of sodium chloropalladate were used instead of palladium chloride, and except that the amount of NaOH was now 5.5 g and that of potassium acetate was 35.1 g.

The prepared catalyst contained 1.0% by weight of Pd, 0.4% by weight of Au and 2.8% by weight of K. The coat thickness was 1.3 to 1.6 mm.

Testing was carried out in a Berty reactor at 152° C. using a gas mixture of 8% by volume of $O_2$, 37.5% by volume of $C_2H_4$, 15.7% by volume of HOAc and 38.8% by volume of $N_2$; the results are shown in Table 1.

EXAMPLE 1a 16 g of palladium acetate, 25 g of cadmium acetate and 25.3 g of potassium acetate were dissolved in 58.8 ml of acetic acid (solution volume=15% of the pore volume) at 65° C. and the highly viscous solution was introduced into a vessel preheated to 65° C. 1 l of catalyst carrier was likewise heated to 65° C. in a temperature-controllable mixing drum and was thoroughly mixed at a speed of 150 revolutions per minute. Within one hour, the impregnating solution was applied to the catalyst carrier by means of an ultrasonic atomizer (100 kHz).

Thereafter, drying was carried out as in Comparative Example 1. The prepared catalyst contained 1.4% by weight of Pd, 1.8% by weight of Cd and 1.9% by weight of K. The coat thickness was 0.5 mm.

Testing was carried out as in Comparative Example 1. The results are shown in Table 2.

EXAMPLE 1b

The catalyst preparation was carried out as in Example 1a, except that 25.3 g of palladium acetate and 137.2 ml of acetic acid were now used instead of 16 g of palladium acetate and 60 ml of acetic acid (solution volume m 35% of the pore volume).

The catalyst contained 2.3% by weight of palladium, 1.8% by weight of Cd and 1.9% by weight of K. The coat thickness was 0.8 min.

Testing was carried out as in Comparative Example 1. The results are shown in Table 2.

EXAMPLE 2

The catalyst preparation is carried out as in Example 1b, except that 4.3 g of barium acetate were now used instead of cadmium acetate. The prepared catalyst contained 2.3% by weight of Pd, 0.4% by weight of Ba and 1.9% by weight of K, and the coat thickness was 0.8 mm.

Testing was carried out as in Comparative Example 1. The results are shown in Table 2.

EXAMPLE 3

13.8 g of sodium chloropalladate and 4.0 g of tetrachloroauric acid were dissolved in 78.4 ml of water (solution volume=20% of the pore volume). The solution was applied to 1 l of catalyst carrier at room temperature in the course of one hour by means of an ultrasonic atomizer (100 kHz); drying was then carried out in a hot air stream at 150° C. Thereafter, a solution of 5.5 g of NaOH in 78.4 ml of water was applied to the impregnated carrier by means of the ultrasonic atomizer in order to precipitate palladium and cadmium, analogously to Comparative Example 3. Said carrier was then washed chloride-free and dried, according to Comparative Example 3. It was then reduced with $B_2$, impregnated with 35.1 g of potassium acetate in 392 ml of water and dried with hot air at 150° C.

The prepared catalyst contained 1.0% by weight of Pd, 0.4% by weight of Au and 2.8% by weight of K, the coat thickness being 0.7 mm.

Testing was carried out as in Comparative Example 4; the results are shown in Table 2.

|  | Performance [g/h] | Spec. performance (*) | Vinyl acetate content (% by weight) in the condensed reactor outlet gas | Selectivity [%] |
| --- | --- | --- | --- | --- |
| Comp. Example 1 (Pd/K/Cd □) | 813 | 70.7 | 25.7 | 94.3 |
| Comp. Example 2 (Pd/K/Ba □) | 827 | 71.9 | 25.9 | 92.8 |
| Comp. Example 3 (Pd/K/Cd #) | 735 | 98.0 | 24.0 | 91.4 |
| Comp. Example 4 (Pd/K/Au #) | 710 | 142.0 | 22.6 | 89.3 |

(*) Grams of vinyl acetate per gram of palladium per hour
□ Impregnated throughout
Coated catalyst according to German patent application P 41 20 492.1

TABLE 2

|  | Performance [g/h] | Spec. performance (*) | Vinyl acetate content (%) in the condensed reactor outlet gas | Selectivity [%] |
| --- | --- | --- | --- | --- |
| Example 1a (Pd/K/Cd) | 760 | 108.6 | 25.0 | 98.0 |
| Example 1b (Pd/K/Cd) | 915 | 79.6 | 33.0 | 96.3 |
| Example 2 (Pd/K/Ba) | 917 | 79.7 | 33.1 | 95.7 |
| Example 3 (Pd/K/Au) | 740 | 148.0 | 24.2 | 90.0 |

(*) Grams of vinyl acetate per gram of palladium per hour

We claim:

1. A method for the preparation of vinyl acetate in the gas phase comprising contacting a supported catalyst containing palladium, potassium and cadmium on a carrier material, obtainable by a process which comprises dissolving salts of palladium, of potassium and of cadmium in a suitable solvent, atomizing the solution by ultrasonics, impregnating the carrier material at least once with the atomized solution and drying it after each impregnation, the atomizer solution for each impregnation being at least 5 to at most 60% of the pore volume of the carrier material and the period from the beginning of each impregnation to the beginning of the subsequent drying being so short that after the end of the final drying, a coat of at least 5 to at most 60% of the volume of the carrier particles contains said salts: with ethylene, acetic acid and oxygen or oxygen-containing gases.

2. The method as claimed in claim 1 wherein the solution for each impregnation with the Pd, K and Cd salts is at least 15 to at most 40% of the pore volume, and the period from the beginning of each impregnation to the beginning of the subsequent drying being so short that after the end of the final drying, a coat of at least 15 to at most 40% of the volume of the carrier particles contains said salts.

3. A method for the preparation of vinyl acetate in the gas phase comprising contacting a supported catalyst containing palladium, potassium and barium on a carrier material, obtained by a process which comprises dissolving salts of palladium, of potassium and of barium in a suitable solvent, atomizing the solution by ultrasonics, impregnating the carrier material at least once with the atomized solution and drying it after each impregnation, the solution for each impregnation being at least 15 to at most 80% of the pore volume of the carrier material and the period from the beginning of each impregnation to the beginning of the subsequent drying being so short that after the end of the final drying, a coat of at least 15 to at most 80% of the volume of the carrier particles contains said salts; with ethylene, acetic acid and oxygen or oxygen-containing gases.

4. The method for the preparation of vinyl acetate as claimed in claim 3 wherein the solution for each impregnation with the Pd, K and Ba salts is at least 25 to at most 40% of the pore volume, and the period from the beginning of each impregnation to the beginning of the subsequent drying being so short that after the end of the final drying, a coat of at least 25 to at most 40% of the volume of the carrier particles contains said salts.

5. A method for the preparation of vinyl acetate in the gas phase comprising contacting a supported catalyst containing palladium, potassium and gold on a carrier material, obtained by a process which comprises dissolving salts of palladium, of potassium and of gold in a suitable solvent, atomizing the solution by ultrasonics, impregnating the carrier material at least once with the atomized solution and drying it after each impregnation, the solution volume for each impregnation being at least 5 to at most 80% of the pore volume of the carrier material and the period from the beginning of each impregnation to the beginning of the subsequent drying being so short that after the end of the final drying, a coat of at least 5 to at most 80% of the volume of the carrier particles contains said salts: with ethylene, acetic acid and oxygen or oxygen-containing gases.

6. The method for the preparation of vinyl acetate as claimed in claim 5 wherein the solution volume for each impregnation with the Pd, K and Au salts is at least 15 to at most 50% of the pore volume, and the period from the beginning of each impregnation to the beginning of the subsequent drying being so short that after the end of the final drying, a coat of at least 15 to at most 50% of the volume of the carrier particles contains said salts.

* * * * *